US009617197B2

(12) United States Patent
Shim et al.

(10) Patent No.: US 9,617,197 B2
(45) Date of Patent: Apr. 11, 2017

(54) COMPOSITIONS AND METHODS FOR TREATING INFLAMMATORY DISEASES

(75) Inventors: Yun Michael Shim, Charlottesville, VA (US); Mikell Paige, Fairfax, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 13/814,087

(22) PCT Filed: Aug. 4, 2011

(86) PCT No.: PCT/US2011/046544
§ 371 (c)(1),
(2), (4) Date: May 28, 2013

(87) PCT Pub. No.: WO2012/018980
PCT Pub. Date: Feb. 9, 2012

(65) Prior Publication Data
US 2013/0236532 A1    Sep. 12, 2013

Related U.S. Application Data

(60) Provisional application No. 61/730,635, filed on Aug. 4, 2010.

(51) Int. Cl.
| A01N 31/14 | (2006.01) |
| A61K 31/075 | (2006.01) |
| C07C 43/205 | (2006.01) |
| A61K 9/08 | (2006.01) |
| A61K 31/085 | (2006.01) |
| A61K 31/357 | (2006.01) |
| A61K 31/385 | (2006.01) |
| A61K 31/415 | (2006.01) |
| A61K 31/4192 | (2006.01) |
| A61K 31/53 | (2006.01) |
| A61K 47/40 | (2006.01) |
| A61K 47/48 | (2006.01) |
| B82Y 5/00 | (2011.01) |

(52) U.S. Cl.
CPC .............. *C07C 43/205* (2013.01); *A61K 9/08* (2013.01); *A61K 31/085* (2013.01); *A61K 31/357* (2013.01); *A61K 31/385* (2013.01); *A61K 31/415* (2013.01); *A61K 31/4192* (2013.01); *A61K 31/53* (2013.01); *A61K 47/40* (2013.01); *A61K 47/48969* (2013.01); *B82Y 5/00* (2013.01)

(58) Field of Classification Search
None
See application file for complete search history.

(56) References Cited

U.S. PATENT DOCUMENTS

| 5,185,377 A | 2/1993 | Schewe et al. |
| 6,110,944 A * | 8/2000 | Chen et al. ................ 514/330 |
| 6,365,634 B1 | 4/2002 | Russell et al. |
| 6,919,348 B2 | 7/2005 | Wei |
| 2002/0086853 A1* | 7/2002 | Cherney .............. C07D 275/03 514/79 |
| 2005/0014704 A1 | 1/2005 | Frick et al. |
| 2006/0120967 A1 | 6/2006 | Namburi et al. |
| 2007/0066820 A1 | 3/2007 | Sandanayaka et al. |
| 2007/0208087 A1 | 9/2007 | Sanders et al. |
| 2008/0033024 A1* | 2/2008 | Sandanayaka et al. ...... 514/365 |
| 2009/0012041 A1* | 1/2009 | Cataldo et al. ................. 514/58 |

FOREIGN PATENT DOCUMENTS

| CN | 103338767 A | 10/2013 |
| JP | H10512848 A | 12/1998 |
| JP | 4257517 B2 | 4/2009 |
| JP | 2011505341 A | 2/2011 |
| JP | 2013532734 A | 8/2013 |
| WO | WO-9611192 A1 | 4/1996 |
| WO | WO-2007048645 A2 | 5/2007 |
| WO | WO-2007078335 A2 | 7/2007 |
| WO | WO-2008156721 A1 | 12/2008 |
| WO | WO-2009067600 A2 | 5/2009 |
| WO | WO-2012018980 A2 | 2/2012 |
| WO | WO-2012018980 A3 | 2/2012 |

OTHER PUBLICATIONS

Jiang et al., Bioorganic & Medicinal Chemistry Letters, 2008, 18, 6549-6552.*
Inflammation and Arthritis, WebMD, 2012.*
"International Application Serial No. PCT/US2011/046544, International Search Report mailed Mar. 12, 2012", 4 pgs.
"International Application Serial No. PCT/US2011/046544, Written Opinion mailed Mar. 12, 2012", 8 pgs.
Jiang, X., et al., "Activation and inhibition of leukotriene A4 hydrolase aminopeptidase activity by diphenyl ether and derivatives", Bioorg Med Chem Lett., 18(24), (Dec. 15, 2008), 6549-52.
Penning, T. D, et al., "Structure-activity relationship studies on 1-[2-(4-Phenylphenoxy)ethyl]pyrrolidine (SC-22716), a potent inhibitor of leukotriene A(4) (LTA(4)) hydrolase", J Med Chem., 43(4), (Feb. 24, 2000), 721-35.
"International Application Serial No. PCT/US2011/046544, International Preliminary Report on Patentability mailed Feb. 14, 2013", 10 pgs.
"European Application Serial No. 11815305.5, Extended European Search Report mailed Jan. 24, 2014", 18 pgs.
De Oliveira, E. O, et al., "Effect of the leukotriene A4 hydrolase aminopeptidase augmentor 4-methoxydiphenylmethane in a preclinical model of pulmonary emphysema", Bioorg Med Chem Lett., 21(22), (Nov. 15, 2011), 6746-50.
Sandanayaka, V., et al., "Discovery of 4-[(2S)-2-{[4-(4-chlorophenoxy)phenoxy]methyl}-1-pyrrolidinyl]butanoic acid (DG-051) as a novel leukotriene A4 hydrolase inhibitor of leukotriene B4 biosynthesis.", J Med Chem., 53(2), (Jan. 28, 2010), 573-85.

(Continued)

Primary Examiner — Dennis Heyer
Assistant Examiner — Daniel M Podgorski
(74) Attorney, Agent, or Firm — Schwegman Lundberg & Woessner, P.A.

(57) ABSTRACT

The present application discloses compositions and methods useful for treating and preventing inflammation associated with inflammatory diseases and disorders.

19 Claims, 9 Drawing Sheets

(56) References Cited

OTHER PUBLICATIONS

"Japanese Application Serial No. 2013-523329, Office Action mailed Jul. 1, 2015", w/ English Translation, 14 pgs.

Askonas, Leslie J., et al., "Pharmacological Characterization of SC-57461A (3-[Methyl[3-[4-(phenylmethyl)phenoxy]propyl]amino]propanoic Acid HCI), a Potent and Selective Inhibitor of Leukotriene A4 Hydrolase I: In Vitro Studies", The Journal of Pharmacology and Experimental Therapeutics vol. 300, No. 2, (Nov. 2, 2001), 577-582.

Jiang, X., et al., "Activation and inhibition of leukotriene A4 hydrolase aminopeptidase activity by diphenyl ether and derivatives", Bioorganic & Medicinal Chemistry Letters, vol. 18, (2008), 6549-6552.

"Chinese Application Serial No. 201180047949.1, Office Action mailed Jun. 11, 2014", With English Translation, 15 pgs.

Davies, D. R, et al., "Discovery of leukotriene A4 hydrolase inhibitors using metabolomics biased fragment crystallography", J Med Chem., 52(15), (Aug. 13, 2009), 4694-715.

Davies, D. R, et al., "Supporting Information—Discovery of leukotriene A4 hydrolase inhibitors using metabolomics biased fragment crystallography", J Med Chem., 52(15), (Aug. 13, 2009), 4694-715.

Thunnissen, M. M, et al., "Crystal structure of human leukotriene A(4) hydrolase, a bifunctional enzyme in inflammation", Nat Struct Biol., 8(2), (Feb. 2001), 131-5.

Wang, Jing, et al., "Research and progress of the application of cyclodextrin in mucosal administration system", China Pharmacy vol. 19, Issue 13, No English Abstract for this reference available, (Dec. 31, 2008), 1019-1021.

"Chinese Application Serial No. 201180047949.1, Office Action mailed Apr. 30, 2015", 5 pgs.

"Chinese Application Serial No. 201180047949.1, Office Action mailed Jan. 19, 2016", 9 pgs.

"Japanese Application Serial No. 2013-523329, Examiners Decision of Final Refusal mailed Mar. 8, 2016", 16 pgs.

"Chinese Application Serial No. 201180047949.1, Response filed Sep. 14, 2015 to Office Action mailed Apr. 30, 2015", w/ English Claims, 16 pgs.

"Japanese Application Serial No. 2013-523329, Response filed Dec. 2, 2015 to Office Action mailed Jul. 1, 2015", w/ English Claims, 11 pgs.

Askonas, Leslie J., et al., "Pharmacological characterization of SC-57461A (3-[methyl[3-[4-(phenylmethyl)phenoxy] propyl]amino]propanoic acid HCI), a potent and selective inhibitor of leukotriene A(4) hydrolase I: in vitro studies", J Pharmacol Exp Ther. 300(2), (Feb. 2002), 577-582.

Penning, Thomas D., et al., "Structure-Activity Relationship Studies on 1-[2-(4-Phenylphenoxy)ethyl]pyrrolidine (SC-22716), a Potent Inhibitor of Leukotriene A4 (LTA4) Hydrolase", J. Med. Chem. 2008, vol. 43 No. 4, (2000), 721-735.

"European Application Serial No. 11815305.5, Communication pursuant to Article 94(3) EPC mailed Jul. 22, 2016", 8 pgs.

"Chinese Application Serial No. 201180047949.1, Office Action mailed Oct. 10, 2016", W/ English Translation, 20 pgs.

\* cited by examiner

COMPOSITIONS AND METHODS FOR TREATING INFLAMMATORY DISEASES

CROSS-REFERENCE TO RELATED APPLICATIONS

The present application is a U.S. National Stage Filing under 35 U.S.C. 371 from International Patent Application Serial No. PCT/US2011/046544, filed on Aug. 4, 2011, and published on Feb. 9, 2012 as WO 2012/018980 A2, which claims the benefit of the filing date of U.S. application Ser. No. 61/370,635, filed on Aug. 4, 2010, the benefit of priority of each of which is claimed hereby, and each of which are incorporated by reference herein in its entirety.

STATEMENT REGARDING FEDERALLY SPONSORED RESEARCH OR DEVELOPMENT

This invention was made with government support under Grant No. K08HL091127-01, awarded by The National Institutes of Health. The government has certain rights in the invention.

BACKGROUND

The family of metabolites derived from the 5-lipoxygenase pathway (a.k.a. leukotrienes) has been characterized as pro-inflammatory deleterious molecules in numerous diseases (Shim et al., 2006; Vargaftig et al., 2003; Sayers et al., 2003; Peters-Golden et al., 2002; Avis et al., 2001; Profita et al., 2000; Wilborn et al., 1996; Sperling et al, 1992). Two major groups of downstream 5-lipoxygenase metabolites are cysteinyl leukotrienes (cLTs) (Capra et al., 2006; Asakura et al., 2004; Espinosa et al., 2003; Chibana et al., 2003; Ellis et al., 1994) and leukotriene $B_4$ ($LTB_4$). A rate-limiting enzyme for $LTB_4$ synthesis, $LTA_4$ hydrolase ($LTA_4H$), has two catalytic activities, epoxyhydrolase activity ($LTA_4H$ EH activity), which channels upstream 5-lipoxygenase metabolites and synthesizes $LTB_4$ (Stenson et al., 1984; Maycock et al., 1982), and aminopeptidase activity ($LTA_4H$ AP activity), which cleaves the N-terminus of different peptides. $LTB_4$ exerts its biological effects through two known receptors, $LTB_4$ receptor 1 and 2 (Del Prete et al., 2007; Pettersson et al., 2005; Gaudreault et al., 2005; Scott et al., 2004; Tarlowe et al., 2003; Jackson et al., 1999; Hullot et al., 1997; Showell et al., 1995; Fretland et al., 1995; Lawrence et al., 1994; Fretland et al., 1989).

To date, $LTB_4$ has been considered a biomolecule that plays a major role in the chemotaxis and/or activation of neutrophils, monocytes, dendritic cells and lymphocytes at sites of inflammation. Therefore, over-production of $LTB_4$ has been correlated with tissue damage and poor outcomes in diseases associated with neutrophilic and/or monocytic abnormal inflammation, diseases such as asthma (Turner et al., 1996; Radeau et al., 1990; Wardlaw et al., 1989), chronic obstructive pulmonary disease (COPD) (Profita et al., 2005; Hubbard et al., 1991; Tanno et al., 1988; O'Driscoll et al., 1984), cystic fibrosis (Lawrence et al., 1994; Carpagnano et al., 2003; Lawrence et al., 1993; Lawrence et al., 1992; Cromwell et al., 1982), inflammatory bowel diseases (Bouchelouche et al., 1995; Nielsen et al., 1987; Lobos et al., 1987), coronary artery disease (Linsel-Nitschke et al., 2008; Topol et al., 2006), acute respiratory distress syndrome (ARDS) and acute lung injury (ALI) (Hicks et al., 2010; Loick et al., 1994; Sun et al., 1990; Sprague et al., 1990; Goldman et al., 1986), the common cold (Widegren et al., 2011; Kostikas et al., 2005; Callan et al, 1988), and inflammatory arthritis (Senoh et al., 1993; Sprague et al., 1989; Mehta et al., 1989; Mehta et al., 1987). Subsequently, pharmaceutical strategies included attempt to either inhibit production of $LTB_4$ (including agents that provide for complete inhibition of $LTA_4H$ activities) or antagonize $LTB_4$ receptors at local tissues. However, several large pharmaceutical studies with those agents yielded either conflicting or insignificant outcomes in human subjects (Diaz-Gonzalez et al., 2007; Hawkey et al., 1997; Roberts et al., 1997; Schmitt-Groho et al., 2005).

SUMMARY OF THE INVENTION

The present invention provides compounds and compositions that target AP activity, e.g., the AP activity of $LTA_4H$, to alter inflammatory pathways, and thereby alter inflammatory reactions, diseases and/or tissue remodeling. In one embodiment, the invention provides compounds and compositions to prevent, inhibit or treat inflammatory diseases including but not limited to chronic obstructive pulmonary disease (COPD), asthma, cystic fibrosis, inflammatory bowel disease, coronary artery disease, the common cold, acute respiratory distress syndrome/acute lung injury, influenza related pneumonia, and inflammatory arthritis. Although $LTA_4H$ EH activity hydrolyzes $LTA_4$ to synthesize $LTB_4$, which is considered as a disease—causing pathogenic process, the aminopeptidase activity of $LTA_4H$ ($LTA_4H$ AP) is considered to modulate and assist in the resolution of inflammation. Therefore, a compound that alters AP activity may alter inflammatory reactions (acute or chronic) and be employed to prevent, inhibit and/or treat inflammatory diseases.

Without wishing to be bound by any particular theory, it is hypothesized that at least some of the pharmaceutical failures to date targeting the $LTA_4H$ enzyme activity may have been the result of indiscriminate inhibition of $LTA_4H$ AP activity in addition to inhibition of $LTA_4H$ EH activity. Inhibition of $LTA_4H$ AP activity would inhibit the resolution of deleterious inflammation, thereby promoting inflammation. The competing outcomes of the inhibition of the two catalytic activities of $LTA_4H$ may reduce or eliminate any beneficial effects, and paradoxically cause harmful effects, from attempts to inhibit $LTA_4H$.

Exaggerated levels of the leukotriene $B_4$ ($LTB_4$) frequently coexist at sites of inflammation and tissue remodeling. Significant levels of $LTB_4$ were detected in human lung tissues with emphysema compared with lungs without emphysema (9,497±2,839 vs. 4,142±1,173 pg/mL, n=9 vs. 10, P=0.04). To further determine the biological role of $LTB_4$ in the pathogenesis of emphysema, the lungs of wild-type (WT) and $LTA_4$ hydrolase-/-mice ($LTB_4$ deficient, $LTA_4H$-/-) exposed to intranasal elastase or vehicle control were compared. Intranasal elastase administration induced the accumulation of $LTB_4$ in the lungs and caused progressively worsening of emphysema between 14 and 28 days after elastase exposure in WT mice but not in $LTA_4H$-/- mice. Premortem physiology documented increased lung compliance in elastase-exposed WT mice compared with elastase-exposed $LTA_4H$-/- mice as measured by Flexivent (0.058±0.005 vs. 0.041±0.002 mL/cmH$_2$O pressure). Postmortem morphometry documented increased total lung volume and alveolar sizes in elastase-exposed WT mice compared with elastase-exposed $LTA_4H$-/- mice as measured by volume displacement and alveolar chord length assessment. Even though elastase-exposed $LTA_4H$-/- mice were found to have significantly milder emphysema as compared to elastase-exposed WT mice, elastase-exposed LTA$_4$H−/− mice were paradoxically found to have significantly delayed influx (increased infiltration) of CD45(high)CD11b(high)Ly6G(high) leukocytes compatible with neutrophils compared with elastase-exposed WT mice. This led to a speculation that the null mutation in the LTA$_4$H−/− mice is not entirely beneficial, and so apparently there is some mechanism in LTA$_4$H−/− mice that promotes resolution of neutrophilic inflammation, and that mice that are LTA$_4$H EH−/− and LTA$_4$H AP+/+may have an intermediate phenotype, e.g., are less susceptible to/are protected from elastase-induced emphysema. Together, these findings demonstrated that LTA$_4$H enzyme and LTB$_4$ played an important role in regulating the pathogenesis of pulmonary emphysema associated with neutrophilic pulmonary inflammation. Thus, as described hereinbelow, animal modeling of pulmonary emphysematous COPD was used to test the effects of inhibition or augmentation of LTA$_4$H AP activity on the severity of pulmonary emphysema in mice.

Jiang et al. (2008) showed that 1-methoxy-4-phenoxybenzene upregulates LTA$_4$H AP activity, however, as described below, this molecule proved to be unsuitable for in vivo characterization because of chemical instability in pH 6.7 buffer and extreme toxicity, causing greater than 85% mortality in murine pre-clinical models. However, as discussed below, a methylene group replacement of the central oxygen atom resulted in a molecule (4-methoxydiphenylmethane; MDM) that was stable in pH 6.7 buffer and upregulated the aminopeptidase activity of LTA$_4$H in an enzyme-based assay. The results described herein also show that this bis-aryl methane derivative was bioavailable, e.g., after intra-peritoneal injection of mice with MDM combined with peanut oil. Animals treated with an agent that selectively inhibits LTA$_4$H AP activity produced pulmonary emphysema that was as severe as vehicle treated control animals. On the other hand, animals treated with an agent that augments (or otherwise enhances) LTA$_4$H AP activity, e.g., MDM, produced pulmonary emphysema that was significantly less severe than control animals. Histological assessment of the local lung tissues demonstrated considerably less inflammation in animals treated with an agent that augments LTA$_4$H AP activity as compared to animals treated with an agent that inhibits LTA$_4$H AP activity or control animals.

Thus, the data showed that indiscriminant inhibition of LTA$_4$H AP activity (e.g., with 4-pentoxydiphenylmethane (PDM)) led to deleterious outcomes in an animal model of COPD, a disease in which LTA$_4$H and LTB$_4$ play prominent roles. Although inhibition of LTA$_4$H AP activity may not lead to a beneficial effect in diseases associated with aberrant inflammation, and may potentially have harmful effects in inflammatory diseases, agents that inhibit LTA$_4$H AP activity may be useful to enhance an inflammatory response in humans.

In contrast, selective augmentation of LTA$_4$H AP activity (e.g., with agents including MDM) led to significant beneficial effects in inflammatory diseases found to be associated with the dysregulated functions of the LTA$_4$H. Thus, LTA$_4$H AP activity can be targeted for diagnosis, prognostication, prevention, and/or treatment of inflammatory diseases.

As also described herein, an encapsulated formulation having 2-hydroxypropyl-β-cyclodextrin and a compound that augments or enhances LTA$_4$H AP activity (MDM) was administered to mice by intra-nasal administration. The results showed that this formulation of a bis-aryl methane was also bioavailable. Thus, the invention also provides encapsulating strategies, including those that employ 2-hydroxypropyl-β-cyclodextrin, liposomes, micelles, polymeric encapsulating agents, or other such agents, that can provide for compositions that enhance physiochemical properties of agents that augment or enhance LTA$_4$H AP activity while maintaining the effective pharmaceutical properties.

Therefore, the present invention provides compounds, compositions and methods to target and augment or stimulate LTA$_4$H AP activity, which in turn provides beneficial effects in diseases that are known to be associated with exacerbated inflammatory responses via induction of LTA$_4$H EH activity and/or up-regulation of LTB$_4$ production. According, the invention provides a compounds and compositions having a compound that selectively augments or enhances LTA$_4$H AP activity, and optionally preserves or inhibits LTA$_4$H EH activity.

In one embodiment, the invention provides a method to enhance or augment AP activity in a mammal. The method includes administering to a mammal in need thereof an effective amount of a composition having a compound that enhances or augments AP activity. In one embodiment, the compound has formula (I) AR$^1$-Q-AR$^2$, wherein AR$^1$ and AR$^2$ are independently an optionally substituted aryl or heteroaryl, wherein an aryl is a C6-C10 carbocyclic aromatic mono- or bicyclic ring system and a heteroaryl is a 5-9 membered aromatic mono- or bicyclic ring system comprising at least one heteroatom selected from the set consisting of N, NR$^a$, O, and S(O)$_q$ wherein R$^a$ is H or (C1-C6)alkyl and q=0, 1, or 2; wherein any aryl or heteroaryl is substituted with 0-3 J; J is OR$^b$, halo, alkyl, aryl, or heteroaryl; Q is CR$^a{}_2$; R$^b$ is H or (C1-C3)alkyl; or any pharmaceutically acceptable salt thereof; wherein the compound of formula (I) is optionally in form of an inclusion complex with a macromolecular entity.

Thus, the invention provides compounds, compositions and methods to treat inflammatory diseases such as emphysematous COPD, asthma, cystic fibrosis, inflammatory bowel diseases, coronary artery disease, acute respiratory distress syndrome/acute lung injury, common cold, influenza virus infection, inflammatory arthritis and/or any other diseases found to be associated with dysregulated LTA$_4$H activity. In one embodiment, the present invention encompasses a compound and a composition having a compound that is useful to augment AP activity, for instance, to augment aminopeptidase N activity or LTA$_4$H AP activity, which in turn may be useful to prevent, inhibit or treat the above-mentioned inflammatory diseases in humans.

In one embodiment, the invention provides compositions and methods of using those compositions to prevent, inhibit or treat inflammatory diseases and disorders, such as those described above, by targeting bone marrow, peripheral blood and/or local end organ tissues, by genetically and/or biologically augmenting LTA$_4$H AP activity, e.g., by administering recombinant LTA$_4$H including a mutant LTA$_4$H that has enhanced LTA$_4$H AP activity relative to a WT LTA$_4$H AP. In one embodiment, the invention provides compositions and methods by which LTA$_4$H AP activity is augmented by compositions having compounds described herein, including compounds of formula (I)-(IV), or other compositions having compounds that augment LTA$_4$H AP activity and optionally inhibit LTA$_4$H EH activity. In one embodiment, the invention provides a composition and method which employ MDM to augment or enhance LTA$_4$H AP activity.

In one aspect, the present invention provides compositions and methods for the genetic or biological characterization of LTA$_4$H AP activity from cells and tissues, including, but not limited to, bone marrow, peripheral blood, and/or local end organ tissues, including cells or tissues from a mammal having or suspected of having an inflammatory disease including COPD, emphysema and/or chronic bronchitis, asthma, cystic fibrosis, inflammatory bowel disease, coronary artery disease, acute respiratory distress syndrome/acute lung injury, the common cold, influenza virus infection, inflammatory arthritis and/or any other human disease associated with dysregulated $LTA_4H$ activity. Thus, in one embodiment, a compound that alters $LTA_4H$ AP activity is contacted with a sample from a mammal, and the $LTA_4H$ activity in the sample before and after contact with the compound is compared or is compared to a control (normal) sample.

In one embodiment, the invention provides compositions and methods of using those composition, for diagnosis or prognosticating of inflammatory diseases, such as those described above, by genetically and or biologically characterizing $LTA_4H$ AP activity from cells and tissues, including, but not limited to, bone marrow, peripheral blood, and/or local end organ tissues including biopsies from lung, vascular tissue, joints, or intestine and in nasal/posterior pharyngeal secretions. In one embodiment, it is determined whether a compound alters $LTA_4H$ AP activity without altering $LTA_4H$ EH activity.

In one embodiment, the invention provides compositions and methods to enhance inflammation by employing a compound that inhibits LTA4H AP activity, e.g., the use of 4-pentoxydiphenylmethane (PDM) to inhibit $LTA_4H$ AP activity. In one embodiment, the compound, composition and methods employs a compound that selectively inhibits $LTA_4H$ AP activity, and optionally preserves or inhibits $LTA_4H$ EH activity.

The invention thus provides compounds and compositions for use in medical therapy, including compounds that prevent, inhibit or treat inflammation, optionally in conjunction with other compounds. Also provided is the use of the compounds and compositions for the manufacture of a medicament to prevent, inhibit or treat inflammation.

Further provided are screening assays to identify compounds that selectively augment or enhance $LTA_4H$ AP activity, and preserve $LTA_4H$ EH activity.

DETAILED DESCRIPTION OF THE INVENTION

Definitions

Figure 1:
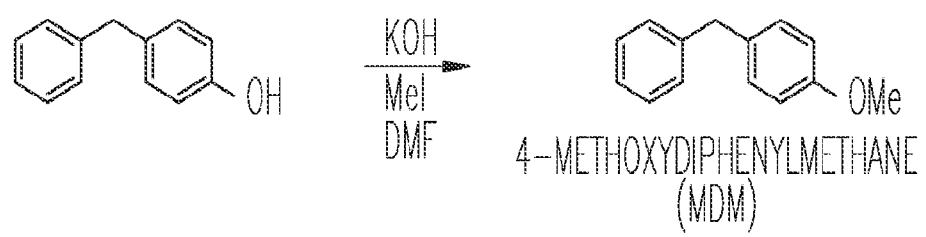
FIG. 1. Synthesis of 4-methoxydiphenylmethane (MDM) and 4-pentoxydiphenylmethane (PDM). Synthesis of MDM was accomplished by treatment of 4-benzyl phenol in dimethylformamide solvent with potassium hydroxide followed by methyl iodide. Synthesis of compound PDM was accomplished by treatment of 4-benzyl phenol in dimethylformamide solvent with potassium hydroxide followed by pentyl iodide.
Figure 1:
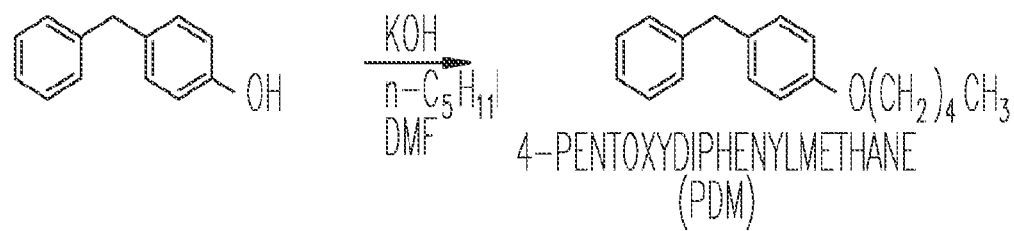

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%. Because dysregulated inflammation is the basis of all human diseases, the present invention encompasses a broad range of uses and a broad range of diseases and disorders.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, goats, and rodents including rabbits, mice, rats and ferrets. Non-mammals include, for example, fish and birds.

The term "disease" or "disorder" or "malcondition" are used interchangeably, and are used to refer to diseases or conditions wherein inflammation plays a role in the biochemical mechanisms involved in the disease or condition.

The expression "effective amount", when used to describe therapy to an individual suffering from a disorder, refers to the amount of a compound or composition of the invention that is effective to prevent or inhibit or otherwise treat inflammation in the individual's tissues where altering the activity of an aminopeptidase target occurs to an extent sufficient to produce a beneficial therapeutic effect.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-n itrobenzyloxycarbonyl, 2-n itrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-n itrobenzyloxycarbonyl, 2-n itrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected. Similarly, a methylenedioxy group can be a substituent when bonded to two adjacent carbon atoms, such as in a phenyl ring.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(═O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—CH$_3$, —CH═CH—CH$_2$—OH, —CH$_2$—CH═N—OCH$_3$, —CH═CH—N(CH$_3$)—CH$_3$, —CH$_2$—CH═CH—CH$_2$—SH, and —CH═CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, e.g., fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. In one embodiment, $(C_x-C_y)$perfluoroalkyl is —$(C_1-C_6)$perfluoroalkyl. In one embodiment, $(C_x-C_y)$perfluoroalkyl is —$(C_1-C_3)$perfluoroalkyl. In one embodiment, $(C_x-C_y)$perfluoroalkyl is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. In one embodiment, $(C_x-C_y)$perfluoroalkylene is —$(C_1-C_6)$perfluoroalkylene. In one embodiment, $(C_x-C_y)$perfluoroalkylene is —$(C_1-C_3)$perfluoroalkylene. In one embodiment, $(C_x-C_y)$perfluoroalkylene is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —$C(O)NR_2$, and —NRC(O)R groups, respectively. Amide groups therefore include but are not limited to primary carboxamide groups (—$C(O)NH_2$) and formamide groups (—NHC(O)H). A "carboxamido" group is a group of the formula $C(O)NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —$OC(O)NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if a group X is described as selected from the set consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

Exemplary Embodiments

This invention relates to the involvement of leukotriene $A_4$ hydrolase ($LTA_4H$) and its epoxyhydrolase ($LTA_4H$ EH) and aminopeptidase ($LTA_4H$ AP) activities, in pathological diseases from exacerbated inflammation. The product of the hydrolase activity of the leukotriene $A_4$ hydrolase is leukotriene $B_4$ ($LTB_4$). $LTB_4$ is an arachidonic acid metabolite, which is produced in the 5-lipoxygenase pathway, is biosynthesized in various cells including mast cells, neutrophils, monocytes, macrophages, lymphocytes and the like, and plays a role as an important mediator in inflammation. $LTB_4$ induces chemotaxis, aggregation and degranulation of leukocytes, accumulation of leukocytes, and accelerates blood-vessel permeability, edema formation and tissue destruction and scarring. Particularly high levels of $LTB_4$ have been detected at lesion sites in inflammatory diseases such as asthma, COPD, cystic fibrosis, inflammatory bowel diseases, coronary artery disease, acute respiratory distress syndrome (ARDS) and acute lung injury (ALI), the common cold, and inflammatory arthritis. Because $LTA_4H$ AP activity may play a substantial role in the resolution of deleterious inflammations (Braber et al., 2011; Gagger et al., 2010; Hardison et al., 2009; Jackson et al., 2011; Snelgrove et al., 2010; Xu et al., 2011), agents that enhance AP activity, optionally in conjunction with inhibition of $LTA_4H$ EH activity, may be particularly useful to prevent, inhibit or treat conditions or diseases associated with inflammation, such as aberrant or abnormal inflammation.

In one embodiment, the invention provides a method to prevent, inhibit or treat one or more symptoms associated with inflammation in a mammal having or suspected of having COPD or emphysema. In one embodiment, a compound that enhances or augments AP activity, for instance, $LTA_4H$ AP activity, or a composition having a biocompatible carrier and a compound that enhances or augments AP activity, such as $LTA_4H$ AP activity, is administered to a mammal. In one embodiment, the compound or composition is administered to the lung or nasal passages, e.g., via inhalation. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into a lung. In one embodiment, the amount administered is effective to decrease or eliminate edema in a lung.

In one embodiment, the invention provides a method to prevent, inhibit or treat one or more symptoms associated with inflammation in a mammal having or suspected of having coronary artery disease. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into a coronary artery, e.g., a coronary artery that is diseased or damaged, e.g., due to interventional procedures.

In one embodiment, the invention provides a method to prevent, inhibit or treat one or more symptoms associated with inflammation in a mammal having or suspected of having rheumatoid arthritis. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is intravenously administered, e.g., by injection. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into a joint. In one embodiment, the amount administered is effective to decrease or eliminate edema in a joint.

In one embodiment, the invention provides a method to prevent, inhibit or treat one or more symptoms associated with inflammation in inflammatory bowel disease in a mammal. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into intestinal tissue. In one embodiment, the amount administered is effective to decrease or eliminate edema in intestinal tissue.

In one embodiment, the invention provides a method to prevent, inhibit or treat one or more symptoms associated with inflammation in a mammal having cystic fibrosis. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is administered to the lung or nasal passages, e.g., via inhalation. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into lung tissue. In one embodiment, the amount administered is effective to decrease or eliminate edema in lung tissue.

In one embodiment, the invention provides a method to prevent, inhibit or treat one or more symptoms associated with inflammation in ARDS (acute respiratory distress syndrome) and ALI (acute lung injury) in a mammal. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is administered to the lung or nasal passages, e.g., via inhalation. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into lung tissue. In one embodiment, the amount administered is effective to decrease or eliminate edema in lung tissue.

In one embodiment, the invention provides a method to prevent, inhibit or treat one or more symptoms associated with inflammation in asthma or the common cold in a mammal. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal. In one embodiment, the compound or composition is administered to the lung or nasal passages, e.g., via inhalation, for instance, using a nasal spray. In one embodiment, the compound or composition is intravenously administered. In one embodiment, the compound or composition is orally administered. In one embodiment, the amount administered is effective to decrease or eliminate $LTA_4H$ associated inflammation. In one embodiment, the amount administered is effective to decrease or eliminate inflammatory cell infiltration into lung tissue. In one embodiment, the amount administered is effective to decrease or eliminate edema in lung tissue.

In one embodiment, the invention provides a method to prevent, inhibit or treat one or more symptoms associated with influenza virus infection in a mammal. In one embodiment, a compound that enhances or augments AP activity, for instance, $LTA_4H$ AP activity, or a composition having a biocompatible carrier and a compound that enhances or augments AP activity, e.g., $LTA_4H$ AP activity, is administered to a mammal orally or by inhalation. In one embodiment, the amount administered is effective to decrease or eliminate inflammatory cell infiltration into lung tissue. In one embodiment, the amount administered is effective to decrease or eliminate edema in lung tissue.

The present invention further embraces isolated compounds of the invention, such as compounds of formulas (I)-(IV). The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. An "isolated compound" may refer to a preparation of a compound of the invention or a mixture of compounds of the invention, which contains the named compound or mixture of compounds of the invention in an amount of at least 10 percent by weight of the total weight. The preparation may contain the named compound or mixture of compounds in an amount of at least 50 percent by weight of the total weight; at least 80 percent by weight of the total weight; and in one embodiment at least 90 percent, at least 95 percent or at least 98 percent by weight of the total weight of the preparation. The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

In one embodiment, a compound of formula (I) is $AR^1$-Q-$AR^2$, wherein $AR^1$ and $AR^2$ are independently an optionally substituted aryl or heteroaryl, wherein an aryl is a C6-C10 carbocyclic aromatic mono- or bicyclic ring system and a heteroaryl is a 5-9 membered aromatic mono- or bicyclic ring system comprising at least one heteroatom selected from the set consisting of N, $NR^a$, O, and $S(O)_q$ wherein $R^a$ is H or (C1-C6)alkyl and q=0, 1, or 2; wherein any aryl or heteroaryl is substituted with 0-3 J; J is $OR^b$, halo, alkyl, aryl, or heteroaryl; Q is $CR^a_2$; $R^b$ is H or (C1-C3)alkyl; or any pharmaceutically acceptable salt thereof; wherein the compound of formula (I) is optionally in form of an inclusion complex with a macromolecular entity.

In various embodiments of formula (I) above, $AR^1$ and $AR^2$ are each independently unsubstituted or substituted phenyl, wherein at least one of $AR^1$ and $AR^2$ is a substituted phenyl. In one embodiment, at least one of $AR^1$ and $AR^2$ is phenyl substituted with alkoxy, alkyl, halo, or heteroaryl. In one embodiment, the alkoxy substituting $AR^1$ or $AR^2$ is methoxy. In one embodiment, the heteroaryl substituting $AR^1$ or $AR^2$ is pyrrolyl or imidazolyl.

In various embodiments of formula (I) above, at least one of $AR^1$ and $AR^2$ is an unsubstituted or substituted heteroaryl group. In one embodiment, both $AR^1$ and $AR^2$ are independently unsubstituted or substituted heteroaryl groups. In one embodiment, each heteroaryl group is independently a pyrrolyl, N-methylpyrrolyl, furyl, thienyl, imidazolyl, triazolyl, pyridinyl, pyridazinyl, or pyrimidinyl group.

In one embodiment, a compound of formula (Ia) is $AR^1$-Q-$AR^2$, wherein $AR^1$ and $AR^2$ are independently an optionally substituted aryl or heteroaryl, wherein an aryl is a C6-C10 carbocyclic aromatic mono- or bicyclic ring system and a heteroaryl is a 5-9 membered aromatic mono- or bicyclic ring system comprising at least one heteroatom selected from the set consisting of N, $NR^a$, O, and $S(O)_q$ wherein $R^a$ is H or (C1-C6)alkyl and q=0, 1, or 2; wherein any aryl or heteroaryl is substituted with 0-3 J; J is $OR^b$, halo, alkyl, aryl, or heteroaryl; Q is $CR^a_2$; $R^b$ is H or (C1-C6)alkyl; or any pharmaceutically acceptable salt thereof; wherein the compound of formula (Ia) is optionally in form of an inclusion complex with a macromolecular entity.

In various embodiments of formula (Ia) above, $AR^1$ and $AR^2$ are each independently unsubstituted or substituted phenyl, wherein at least one of $AR^1$ and $AR^2$ is a substituted phenyl. In one embodiment, at least one of $AR^1$ and $AR^2$ is phenyl substituted with alkoxy, alkyl, halo, or heteroaryl. In one embodiment, the alkoxy substituting $AR^1$ or $AR^2$ is methoxy. In one embodiment, the heteroaryl substituting $AR^1$ or $AR^2$ is pyrrolyl or imidazolyl.

In various embodiments of formula (Ia) above, at least one of $AR^1$ and $AR^2$ is an unsubstituted or substituted heteroaryl group. In one embodiment, both $AR^1$ and $AR^2$ are independently unsubstituted or substituted heteroaryl groups. In one embodiment, each heteroaryl group is independently a pyrrolyl, N-methylpyrrolyl, furyl, thienyl, imidazolyl, triazolyl, pyridinyl, pyridazinyl, or pyrimidinyl group.

In one embodiment, the invention provides a compound of formula (II), compositions having the compound, and methods of using the compound. A compound of formula (II) is

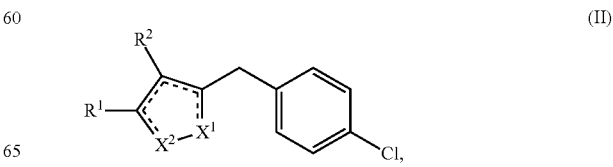
(II)

wherein $X^1$ and $X^2$ are each independently selected N, O, $S(O)_q$, or $CR^3$, dashed lines indicate that each bond can be a single bond or a double bond, provided that the ring comprising X1 and X2 is aromatic; and, $R^1$, $R^2$, and $R^3$ are each independently selected H, alkyl, halogen, aryl, heteroaryl, or alkoxy. In one embodiment, the invention provides a compound of formula (III):

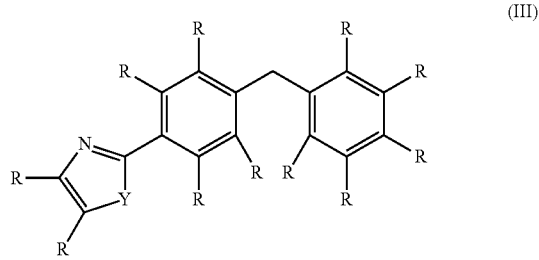

(III)

wherein Y is $CR^a$, NH, or N—$CH_3$; and each independently selected R is H, alkyl, alkoxy, aryl, heteroaryl, or halogen.

In one embodiment, the invention provides a compound of formula (IV):

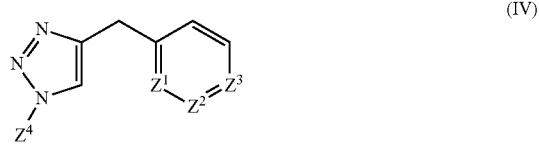

(IV)

wherein $Z^1$, $Z^2$, and $Z^3$ are each independently $CR^a$ or N; and $Z^4$ is H, alkyl, cycyloalkyl, unsubstituted or substituted phenyl, pyrrolyl, pyrrazolyl, imidazolyl, furyl, oxazolyl, isooxazolyl, thienyl, or pyridinyl;

or any pharmaceutically acceptable salt thereof.

Other compounds useful in the compositions of the invention include but are not limited to those disclosed in U.S. Publication 2005/0043378; 2005/0043379; 2005/0085487; 2007/0004695; 2008/0234237; 2009/0111794; 2009/0258854; 2010/0292208 and 2011/0159563, and PCT/US2010/34597; WO2009/126806 (U.S. Publication 2009/040070); WO 2009/058347 (U.S. Publication 2008/012339) or WO 2008/100564 (U.S. Publication 2008/001949), the disclosures of which are incorporated by reference herein.

Compounds useful to alter $LTA_4H$ AP activity may also be useful to alter the activity of other aminopeptidases, e.g., aminopeptidase N (CD13).

Pharmaceutical Compositions

In one embodiment, the invention provides a pharmaceutical composition comprising a compound that enhances or augments $LTA_4H$ AP activity, and a pharmaceutically acceptable excipient. A composition of the invention can provide the compound alone or in combination with another medicament. As set forth herein, compounds include stereoisomers, tautomers, solvates, prodrugs, pharmaceutically acceptable salts and mixtures thereof. Compositions containing a compound can be prepared by conventional techniques, e.g. as described in Remington: *The Science and Practice of Pharmacy*, 19th Ed., 1995, incorporated by reference herein. The compositions can appear in conventional forms, for example capsules, tablets, aerosols, solutions, suspensions or topical applications.

Typical compositions include a compound and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. In one embodiment, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, such as a population that comprises nanoparticles, or can be administered in an extended release form to provide a prolonged storage and/or delivery effect, formed of biodegradable polymers. Nanoparticles range in size from about 1 nm to about 250 nm in mean diameter, about 1 nm to about 200 nm in mean diameter, about 1 nm to about 100 nm in mean diameter, or about 1 nm to about 20 nm in mean diameter. The size of nanoparticles used in a method varies as required by their particular use or application.

The formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, such as aqueous solutions with the active compound dissolved in polyhydroxylated castor oil.

Tablets, dragees, or capsules having talc and/or a carbohydrate carrier or binder or the like are particularly suitable for oral application. In one embodiment, carriers for tablets, dragees, or capsules include lactose, corn starch, and/or potato starch. A syrup or elixir can be used in cases where a sweetened vehicle can be employed.

Pharmaceutical Uses

In various embodiments, the invention provides a method of modulation of inflammation comprising contacting a mammal with an effective amount or concentration of a compound or composition of the invention.

More specifically, the contacting can be in vivo in a human patient. In various embodiments, the amount or concentration of the compound or composition can be effective to selectively modulate AP activity. In other embodiments, an effective amount or concentration of a compound of the invention in the body of a human patient can effectively prevent, inhibit or treat inflammation.

In various embodiments, the invention provides a method of treatment of a condition in a patient for which modulation of inflammation is medically indicated, comprising administering to the patient a compound of any of formulas (I)-(IV), or a composition of the invention in a dose, at a frequency, and for a duration sufficient to provide a beneficial effect to the patient. More specifically, the condition can include asthma, COPD, cystic fibrosis, inflammatory bowel diseases, coronary artery disease, acute respiratory distress syndrome (ARDS) and acute lung injury (ALI), common cold, influenza virus infection, and inflammatory arthritis.

The compounds or compositions of the invention can be administered to a mammal, especially a human in need of such treatment, prevention, elimination, alleviation or amelioration of a condition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, from about 1 to about 2000 mg, or between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 $\mu$g to about 1250 mg, from about 250 $\mu$g to about 500 mg, or from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

The invention will be further described by the following non-limiting examples.

Example 1

To investigate the role that $LTA_4H$ plays in the pathogenesis of human diseases, murine models of elastase-induced pulmonary emphysema (Example 1) and LPS-induced acute lung injury (Example 3) were tested. In order to establish the elastase-dose dependent severity of murine pulmonary emphysema, increasing doses of porcine elastase were instilled into murine lungs of 129J background via the intra-nasal route. Four weeks after elastase was instilled, mouse lungs were harvested en block, inflated with 1% low melting point agarose gel (LMPA) at 25 cm melted 1% LMPA pressure. Lungs were then fixed overnight in formaldehyde. These lungs demonstrated increased total lung volumes corresponding to the increasing doses of intra-nasal elastase by visual inspection and histological inspection of the H&E sections. This confirmed that intra-nasal elastase administration was able to induce pulmonary emphysema in a dose-dependent manner.

The relevance of utilizing the elastase induced murine pulmonary emphysema modeling for the investigation of $LTB_4$ and $LTA_4H$ was confirmed by assessing up-regulation of $LTB_4$ production in these lungs. $LTA_4H$ is considered as a rate-limiting enzyme of the $LTB_4$ biosynthesis, and $LTB_4$ production was up-regulated after intra-nasal elastase exposure. As expected, intra-nasal exposure of the elastase significantly increased detectable amounts of $LTB_4$ in the total lung bronchoalveolar lavage fluid.

Jiang et al. (2008) showed that 1-methoxy-4-phenoxy-benzene upregulates $LTA_4H$ AP activity in vitro. When this molecule was further characterized, we found it to be unsuitable for in vivo characterization because of its chemical instability in pH 6.7 buffer and extreme toxicity, causing greater than 85% mortality in murine pre-clinical models. Subsequently, other bis-aryls were synthesized and tested for modulation of LTA$_4$H AP activity, as discussed below.

Figure 2:
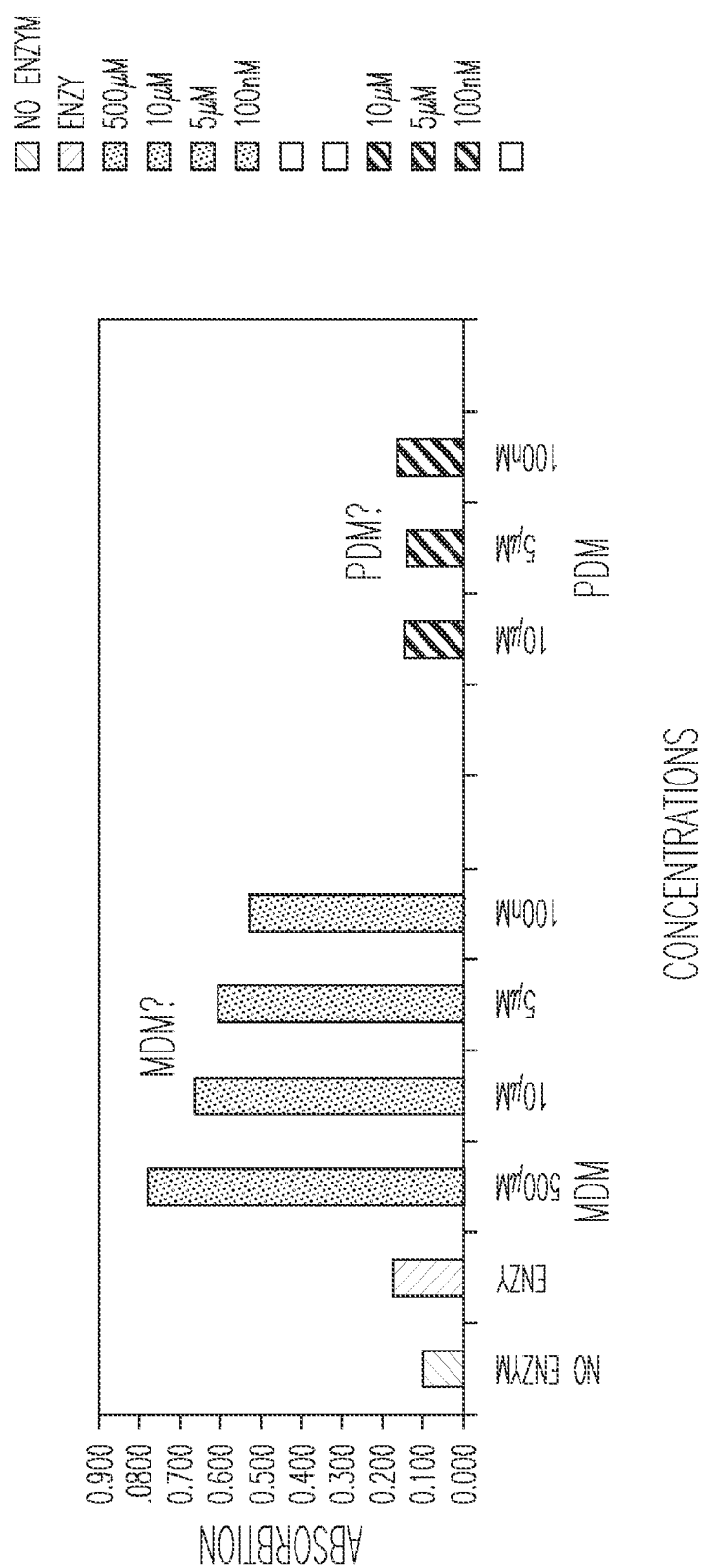
FIG. 2. In vitro aminopeptidase activity assay. The peptidase activity of compounds was determined following the method of Jiang and co-workers (2008). MDM (red) was shown to augment the $LTA_4H$ AP activity, and PDM (blue) was shown to decrease $LTA_4H$ AP activity. No Enzyme=buffer. Enzy=buffer+recombinant $LTA_4H$. 500 μM, 10 μM, 5 μM, and 100 nM=buffer+recombinant $LTA_4H$+Ala-pNA+MDM.

In order to establish the biological roles of LTA$_4$H AP activity in the pathogenesis of pulmonary emphysema, wild type mice were exposed to porcine elastase via the intra-nasal route and then treated with one LTA$_4$H AP activity augmentor (compound 66, MDM), a LTA$_4$H AP activity inhibitor (compound 67, PDM), or vehicle (peanut oil). Synthesis of MDM was accomplished by treatment of 4-benzyl phenol in dimethylformamide solvent with potassium hydroxide followed by methyl iodide (FIG. 1). Synthesis of compound PDM was accomplished by treatment of 4-benzyl phenol in dimethylformamide solvent with potassium hydroxide followed by butyl iodide (FIG. 1). The peptidase activity of the compound was determined following the method of Jiang and co-workers (2008). MDM (red) was shown to augment LTA$_4$H AP activity, and PDM (blue) was shown to decrease LTA$_4$H AP activity (FIG. 2). Jiang et al. (2008) showed that 1-methoxy-4-phenoxybenzene upregulates LTA$_4$H AP activity. When this molecule was further characterized, however, as described below, this molecule proved to be unsuitable for in vivo characterization because of chemical instability in pH 6.7 buffer and extreme toxicity, causing greater than 85% mortality in murine pre-clinical models.

Figure 3:
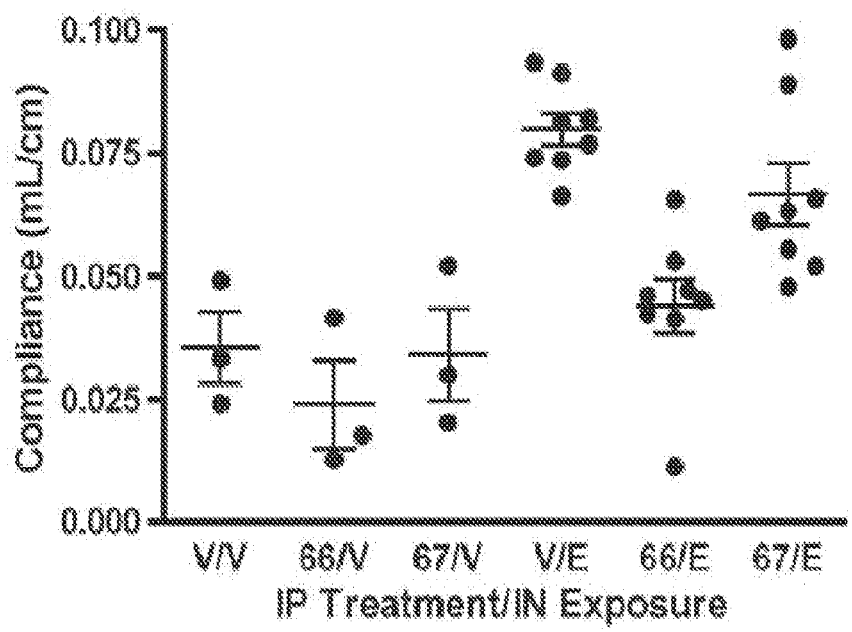
FIG. 3. Pre mortem lung physiology measurement. Live animals were sedated then intubated and ventilated with Flexivent as described in Shim et al. (2010). Lungs with more severe emphysema are more compliant and thus will have greater lung compliance. As expected, lungs treated with PDM had high lung compliance similar to lungs treated with vehicle. Lungs treated with MDM had significantly lower lung compliance as compared to the lungs treated with PDM or vehicle. IN=intra-nasal. IN Vehicle=Phosphate Buffered Saline. Drug Vehicle=Peanut oil. V/V=Vehicle Intra-Nasal Exposure/Vehicle Intra-Peritoneal injection. E=Elastase. 66=MDM. 67=PDM.
Figure 4:
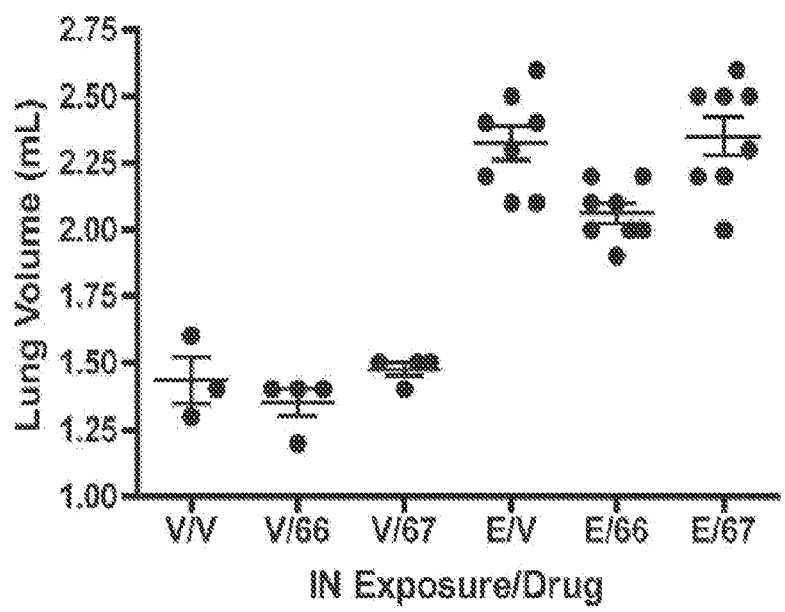
FIG. 4. Post mortem lung volume measurement. All lungs were harvested en block, inflated with same pressure at 25 cm, 1% melted low melting point agarose gel. The total lung volume was measured by volume displacement technique. More severe emphysematous lungs have increased compliance, and therefore total lung volume is larger if emphysema is worse. Lungs of mice (E/66 group) treated with MDM were much less emphysematous as compared to the lungs of mice treated with PDM (E/67 group) or vehicle control (E/V group). IN=intra-nasal. V/V=vehicle intra-nasal exposure/vehicle intra-peritoneal injection. E=Elastase.
Figure 5:
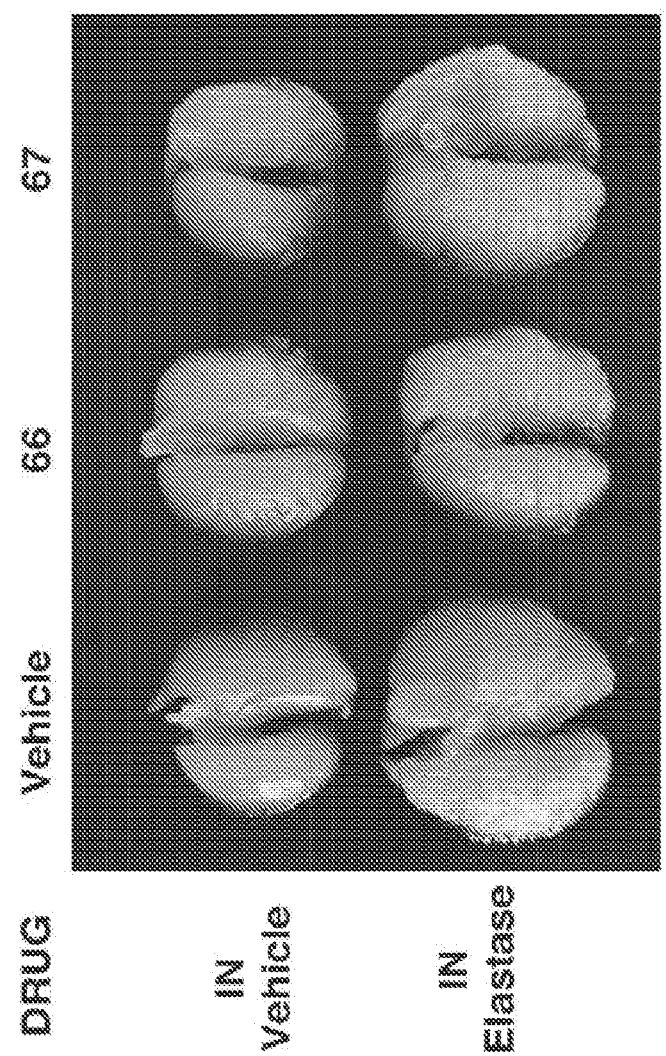
FIG. 5. Gross inspection of the inflated whole lungs. Lungs were harvested en block, inflated with same pressure at 25 cm 1% melted low melting point agarose gel, fixed in para-formaldehyde overnight, and photographed. Lungs with more severe emphysema are more compliant and so are larger in gross appearance. Lungs of mice treated with MDM (compound 66), were much smaller as compared to the lungs of mice treated with PDM (compound 67) or vehicle control. IN=intra-nasal. IN Vehicle=phosphate buffered saline. Drug Vehicle=peanut oil.
Figure 6:
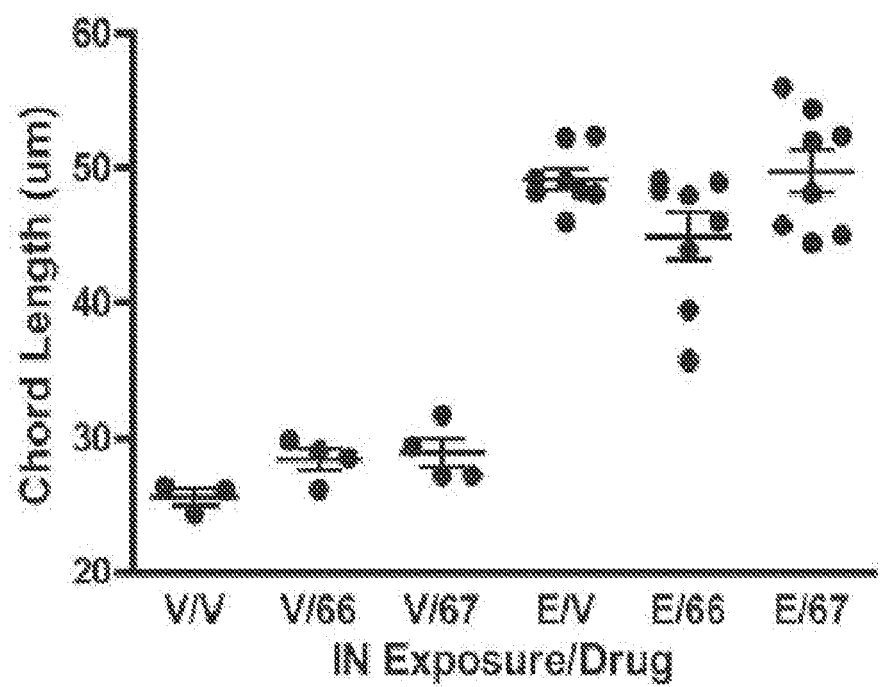
FIG. 6. Lung histology chord length. Para-formaldehyde fixed lung tissues were H&E stained. Consecutive, adjacent photographs were taken for the entire lungs of each animal. These were assessed with a computerized imaging system to measure chord length as described in Shim et al. (2006) and Zheng et al. (2000). Magnitude of chord length from each animal is directly proportional to the sizes of alveoli. Because mouse lungs with more severe emphysema have larger alveoli, the chord length of mouse lungs with more severe emphysema is greater. As expected, chord length was shorter in the mouse lungs of the drug 66 (MDM in peanut oil) (group E/66) treated animals as compared to the mouse lungs of the drug 67 (group E/67) or vehicle (peanut oil) treated animals (group E/V). IN=intra-nasal. V/V=vehicle intra-nasal exposure/vehicle intra-peritoneal injection. E=elastase.

Elastase (0.75 μg elastase per gm mouse weight) was instilled via the intra-nasal route. After 4 weeks, mice were sedated, intubated, and ventilated with Sireq Flexivent to measure lung compliance pre mortem. It was understood that lungs with more severe emphysema would have lost more elasticity, and thus, their lung compliance would be greater when measured by a small animal ventilator (FIG. 3). Once lung compliance was measured, mice were euthanized. Lungs were harvested en block without damaging outer coverings. Once harvested, lungs were inflated with 1% low melting point agarose gel (LMPA) at 25 cm melted 1% LMPA gel pressure. Once inflated, the total lung volumes were measured by volume displacement technique (FIG. 4). It was understood that lungs with more severe emphysema would have lost more elasticity, and thus their lung volume would be greater after being inflated with a uniform pressure. After the total lung volume measurement, lungs were fixed in para-formaldehyde overnight. On the following day, whole lungs were photographed (FIG. 5). Lungs with more severe emphysema would have lost more elasticity, and thus their lungs would be larger after being fixed with para-formaldehyde. The lungs were then paraffin embedded, paraffin sections were H&E stained (FIG. 6A), and morphometry was performed by using NIH ImagePro software and custom written macro string (Shim et al., 2006; Shim et al., 2010; Zheng et al., 2000; Zu et al., 1999). Alveolar intercepts were calculated and averaged from at least 8 animals in each group to yield chord length of each group (FIG. 6B). It was understood that alveoli from lungs with more severe emphysema would be larger after losing more elasticity and thus their chord length of the alveoli would be longer.

These results in combination confirmed that the augmentation of the LTA$_4$H AP activity significantly ameliorated emphysematous destruction of murine lungs while the inhibition of the LTA$_4$H AP activity had no effect on emphysematous destruction of murine lungs.

Example 2

As shown above, the MDM compound is an excellent compound for anti-inflammatory therapy but its water solubility may limit its broad applicability. Of several different approaches and agents such as cyclodextrins, for instance, α, β (e.g., 2-hydroxypropyl-β-cyclodextrin) or γ cyclodextrins (Merkus et al., 1999), liposomes (e.g., formed of phospholipids such as phosphatidylcholine, mixtures of dioleolyl-phosphatidylcholine and or detergent-like molecules, liposomes having sodium deoxycholate, polyethylene glycol, beta-casein-dioleoyl phosphatidylcholine/didecanoyl phosphatidylglycerol (DOPC/DPPG), and polymeric encapsulating agents such as polysaccharide-based polymeric micelles, e.g., dextran-g-polyethylene oxide cetyl ether (Dex-g-PEO-C16) or hydroxypropylcellulose-g-polyethylene oxide cetyl ether (Francis et al., 2005a; Francis et al., 2005b), encapsulation of MDM with 2-hydroxypropyl-β-cyclodextrin ("CDX") was chosen. A higher ratio between CDX and MDM may be more likely to promote enhance water solubility due to a higher probability of shielding hydrophobic MDM from a hydrophilic environment. A lower ratio between CDX and MDM may be more likely to preserve the biological activities of MDM.

a. Encapsulation Method and Equilibrium Solubility Test in Water.

To 5.3 mg (1.0 equivalent) of MDM was added 160.0 mg (4.0 equivalents) of CDX followed by 4.8 mL of water. The suspension was stirred over 12 hours to give a clear solution, which was filtered through a 0.22-micron nylon filter (Restek catalog#26148, lot#19783, 25 mm). The homogeneity of the solution was analyzed by HPLC.

Solubility measurement. Instrumentation: Shimadzu LC20AD pumps (2×), DGU-2A3 degasser, SIL-HTA autosampler, SPD-2A UV-Vis detector, Waters Symmetry C18 5 μm (4.6×250 mm) column (serial#02143702313617). Method: isocratic 80:20 acetonitrile-water at 1.0 mL/min, injection volume=5 μL, monitoring at λ=250 nm.

Results. The encapsulated MDM had a retention time of 6.699 minutes with a peak area of 1,432,521.5±4.4% over 96 hours, suggesting that the solution was homogeneous. Therefore, the compound was considered soluble in the solution at equilibrium.

b. Encapsulation Method and Equilibrium Solubility Test in PBS.

The method was carried out above with phosphate buffer saline (PBS, Ampresco, 20× concentrate, pH7.5; 500 μL of PBS concentrate was added to 9500 μL of water). To 6.0 mg (1.0 equivalents) of MDM was added 180.0 mg (4.0 equivalents) of CDX followed by 5.8 mL of water. The suspension was stirred over 12 hours to give a clear solution, which was filtered through a 0.22-micron nylon filter (Restek catalog#26148, lot#19783, 25 mm). The homogeneity of the solution was analyzed by HPLC.

Solubility measurement. Same as described above.

Results. The encapsulated MDM had a retention time of 6.678 minutes with a peak area of 1,551,513.8±0.9% over 48 hours, suggesting that the solution was homogeneous. Therefore, the compound was considered soluble in the solution at equilibrium.

c. Encapsulation Method and Equilibrium Solubility Test in PBS with Reduced Cyclodextrin Concentration.

The method was carried out as above. To 2.4 mg (1.0 equivalents) of MDM was added 0.035 g (2.0 equivalents) of CDX followed by 2.4 mL of PBS solution. The suspension was stirred over 12 hours to give a clear solution, which was filtered through a 0.22-micron nylon filter (Restek catalog#26148, lot#19783, 25 mm). The homogeneity of the solution was analyzed by HPLC. 5.04 mM Solubility measurement. Same as described above.

Results. The formulation gave a retention time of 6.745 minutes and a peak area of 949,269. The solution was calculated to give a concentration of 5.04 mM. The standard curve showed a concentration of 2.95 mM, suggesting that the equilibrium solution at this 1:2 ratio of MDM:CDX consisted of 59% of the MDM in the homogeneous solution. Therefore, the solubility of the compound with 2 equivalents of CDX was estimated to be 0.59 mg/mL in PBS solution.

Figure 7:
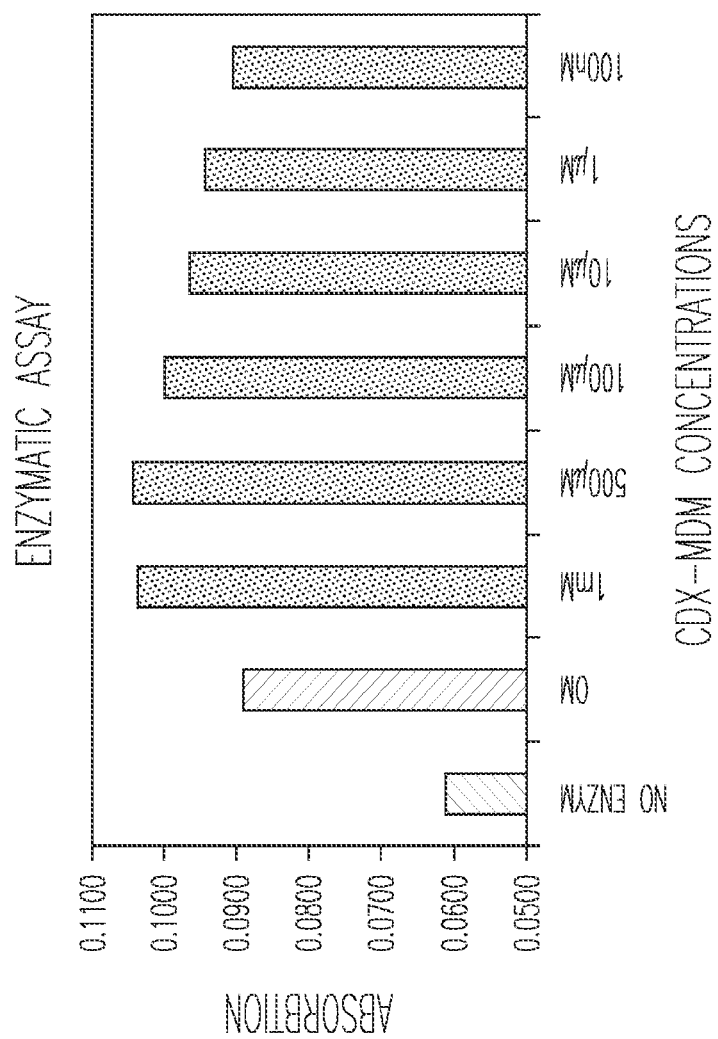
FIG. 7. Biological activities of 2-hydroxypropyl-β-cyclodextrin encapsulated 4-methoxydiphenylmethane ("CDX-MDM"). In order to confirm that the encapsulation strategy by 2-hydroxypropyl-β-cyclodextrin does not alter the biological activity of MDM, an in vitro aminopeptidase activity assay was conducted by treating human recombinant $LTA_4H$ enzyme with CDX-MDM and measuring the $LTA_4H$ AP activity as described in FIG. 2. This in vitro assay confirmed that the encapsulation strategy was able to enhance the physiochemical properties by increasing the water solubility while maintaining original biological activity and stability of MDM. No Enzyme=buffer. 0 M=buffer+recombinant $LTA_4H$+Ala-pNA+no MDM. 500 μM, 10 μM, 5 μM, and 100 nM=buffer+recombinant $LTA_4H$+Ala-pNA+MDM (500 μM, 10 μM, 5 μM, or100 nM).

Thus, in one embodiment, based on the ratio between CDX and MDM is about between 2 CDX:1 MDM and 4 CDX:1 MDM. Both ratios led to homogenous CDX encapsulated MDM (CDX-MDM) in water. In vitro aminopeptidase activity assay was performed to confirm that this composition maintained the AP activity (FIG. 7).

Example 3

In order to show that the augmentation of $LTA_4H$ AP activity may be effective to treat other diseases found to be caused by dysregulated activities of $LTA_4H$, therapeutic benefits of CDX-MDM were tested in a pre-clinical murine disease model other than pulmonary emphysema. For this purpose, the pre-clinical model of LPS induced acute respiratory distress syndrome/acute lung injury was selected to test CDX-MDM based on the important biological roles which the $LTA_4H$ plays in these diseases (Hicks et al., 2010; Loick et al., 1994; Sun et al., 1990; Sprague et al., 1990; Goldman et al., 1986).

Studies were conducted by exposing mice to intra-nasal LPS in order to induce acute respiratory distress/acute lung injury. LPS doses ranging from 0 μg/mouse to 10 μg/mouse (0, 1, 2.5, 5, or 10 μg/50 μL volume per mouse) were considered, and the LPS dose, 5 μg/mouse, was selected. Mouse lungs developed significant leukocyte infiltration mostly consisting of neutrophils and monocytes post intra-nasal LPS. Previous reports have demonstrated substantial up-regulation of the $LTA_4H$ enzymatic activities measured by the levels of $LTB_4$ in the BALF.

Figure 8A:
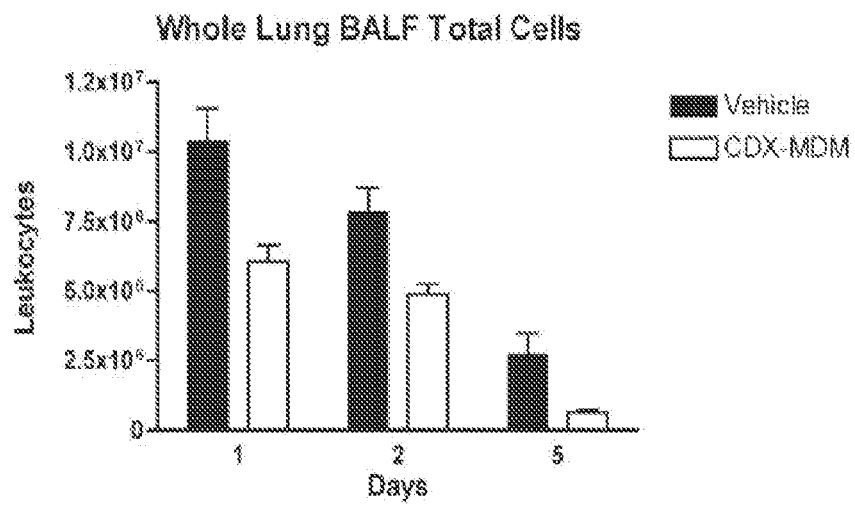
FIGS. 8A-C. Biological effects of CDX-MDM on inflammation in the mouse model of acute lung injury. Enhanced water solubility of the CDX-MDM allows for intra-nasal administration as a route of drug treatment. Mice were exposed to lipopolysaccharide (LPS) via intra-nasal exposure in order to induce acute lung injury. The control group of mice were exposed to intra-nasal LPS dissolved in the vehicle containing 2-hydroxypropyl-β-cyclodextrin in phosphate buffered saline ("CDX-Vehicle") while the experimental group of mice was exposed to LPS dissolved in CDX-MDM in phosphate buffered saline (PBS). Mice were exposed to intra-nasal LPS only on day 0, then mice were exposed to either CDX-Vehicle or CDX-MDM treatments daily for 4 days, after which the number of leukocytes cells in the total lung broncholaveolar lavage fluid ("BALF") was measured) (panel A) as well as neutrophils (panel B) and monocytes (panel C). Mouse lungs treated with the intra-nasal CDX-MDM had significantly fewer inflammatory cells post LPS exposure as compared to the mouse lungs treated with the intra-nasal CDX-Vehicle alone.
Figure 8B:
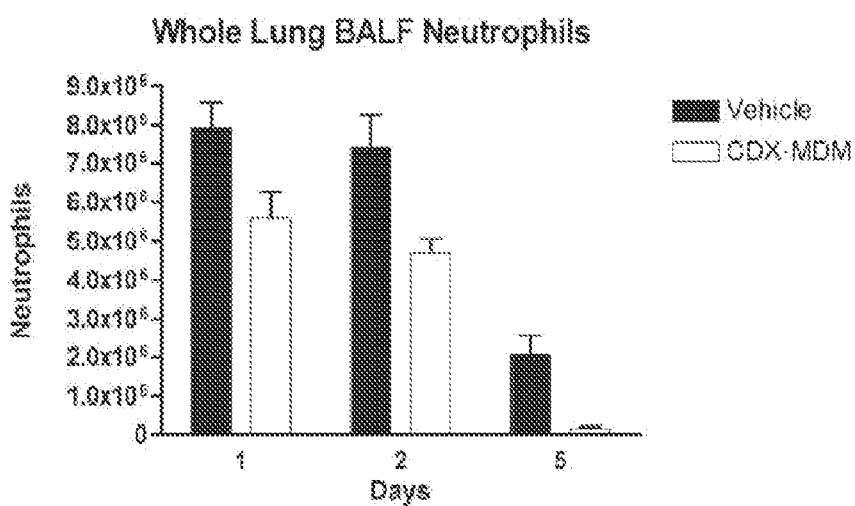
Figure 8C:
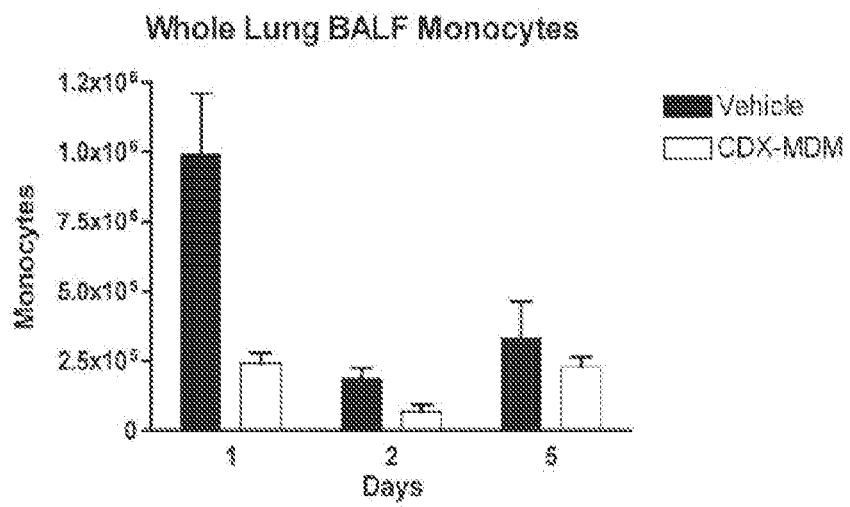
Figure 9:
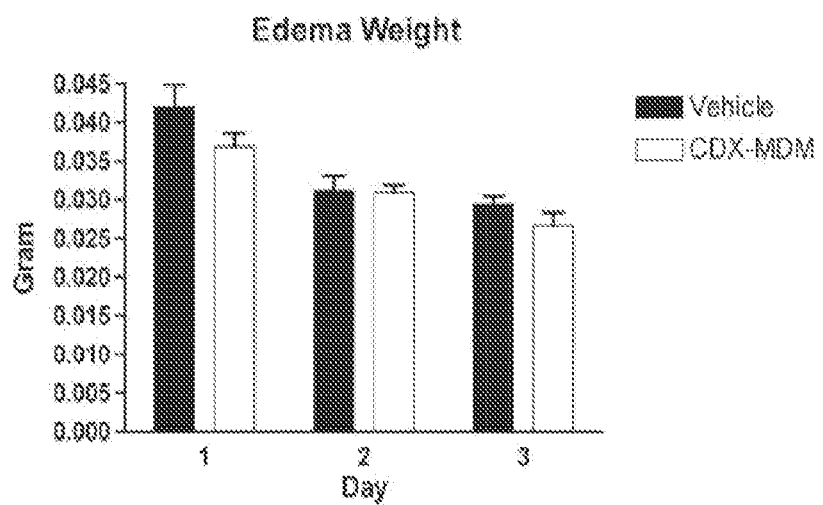
FIG. 9. Effects of the CDX-MDM on pulmonary edema in the mouse model of acute lung injury. Damage from intra-nasal LPS exposure can be assessed by the amount of water accumulation (pulmonary edema) in murine lungs. Mitigated inflammation is expected to result in less damage from LPS exposure. The same lobes of lungs were assessed from mice treated with either CDX-Vehicle alone or CDX-MDM post intra-nasal LPS administration. The amount of pulmonary edema was reflected by the difference of weight between fresh lung tissues and dried lung tissues. As expected, mouse lungs treated with the CDX-MDM accumulated less water post LPS exposure as compared to the CDX-Vehicle treated mouse lungs. This demonstrated that intra-nasal CDX-MDM treatment protected mouse lungs from the intra-nasal LPS induced acute lung injury, likely by mitigating inflammation as demonstrated by the results shown in FIG. 8.
Figure 10:
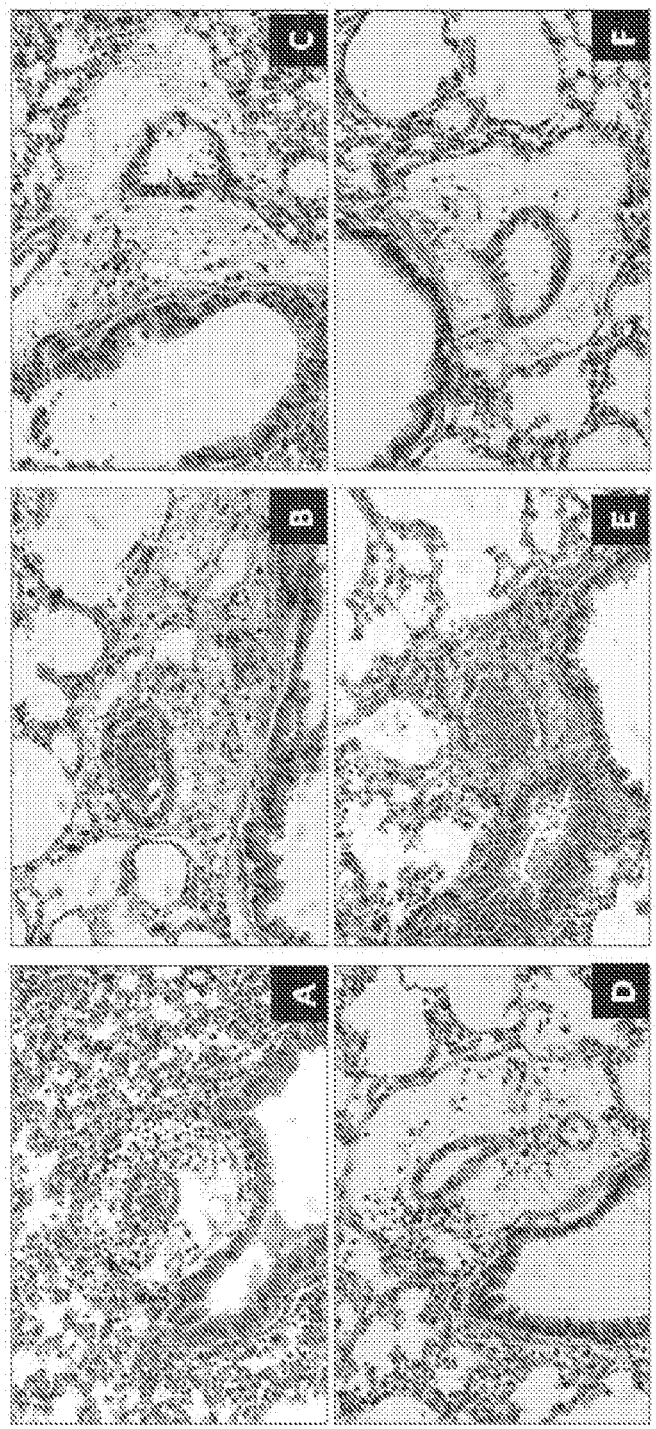
FIGS. 10A-F. Effects of the CDX-MDM on pulmonary damage in the mouse model of acute lung injury. Paraformaldehyde fixed lung tissues were H&E stained. Representative photographs of medium sized peri-bronchial vessels were taken to document the intensity of the leukocyte infiltration into mouse lungs post intra-nasal LPS treated either with CDX-Vehicle or CDX-MDM. As demonstrated by the leukocyte counts in BALF (FIG. 8A), mouse lungs treated with CDX-MDM showed significantly less leukocyte infiltration into lungs post intra-nasal LPS exposure as compared to mouse lungs treated with CDX-Vehicle. H&E stained lung tissue histology demonstrated similar findings in the peri-bronchial vessels at 40× magnification. A) CDX-Vehicle treated lung 1 day post IN LPS. B) CDX-Vehicle treated lung 2 days post IN LPS. C) CDX-Vehicle treated lung 5 days post IN LPS. D) CDX-MDM treated lung 1 day post IN LPS. E) CDX-MDM treated lung 2 days post IN LPS. F) CDX-MDM treated lung 5 days post IN LPS. CDX-Vehicle=2-hydroxypropyl-β-cyclodextrin dissolved in phosphate buffered saline. CDX-MDM=2-hydroxypropyl-β-cyclodextrin encapsulated MDM in phosphate buffered saline. IN=intra-nasal. LPS=lipopolysaccharide at 5 μg/mouse dose in 50 μL volume.

CDX-MDM was instilled into the mouse lungs via intra-nasal route after acute lung injury was induced by intra-nasal LPS exposure. CDX-MDM was prepared by mixing 2 parts of CDX with 1 part of MDM in phosphate buffered water (PBS). One group of animals (n=5-8) was treated daily with the CDX-Vehicle in PBS post intra-nasal LPS exposure, and a second group was treated daily with intra-nasal CDX-MDM post intra-nasal LPS. The CXD-MDM treated mice experienced substantially less inflammation as assessed by the total leukocyte, monocyte and neutrophil counts in the whole lung BALF and by histological evaluation (FIGS. 8 and 10). The beneficial effects of the CDX-MDM were most prominent 5 days after initiating the treatment (FIGS. 8 and 10). Significantly less pulmonary edema was also noted in the CDX-MDM treated mouse lungs as compared to the CDX-Vehicle treated mouse lungs (FIG. 9). This demonstrated that the CDX-MDM treatment was able to mitigate the severity of the acute lung injury from the intra-nasal LPS by alleviating the infiltration of inflammatory cells and pulmonary edema.

Based on the findings described above, bis-aryl methanes and related analogs may be bioavailable upregulators of $LTA_4H$ AP activity. Therefore, compounds having the general scaffold Aryl-CH2-Aryl' may be bioavailable augmentors of the $LTA_4H$ aminopeptidase. For example, aryl can but does not necessarily equal Aryl' and aryl may refer to any mono-, di-, or tri-aromatic ring system, substituted aromatic ring, or fused aromatic ring system, or bioisostere of an aromatic group. A representative example of molecules are shown below:

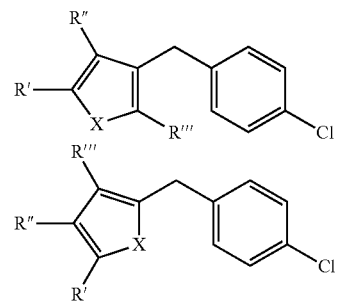

R' = H or OMe
R'' = H or OMe
R''' = H or OMe
X = S, O, NH, or NMe

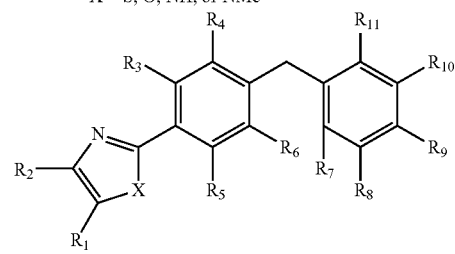

R = H, halogen, OMe, or alkyl
R groups can but do not need to equal each other
X = S, O, NH, or NMe

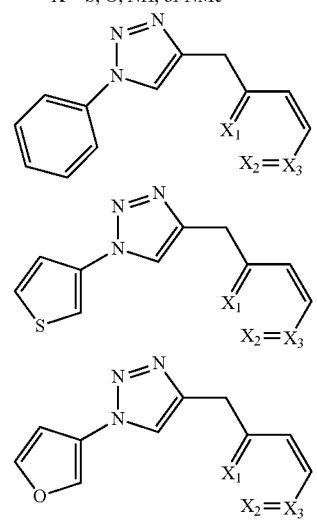

$X_1$ = CH or NH
$X_2$ = CH or NH
$X_3$ = CH or NH

REFERENCES

Asakura et al., J Allergy Clin Immunol, 2004. 114(2): p. 310-5.

Avis et al., Faseb J, 2001. 15(11): p. 2007-9.

Bouchelouche et al., Eur J Gastroenterol Hepatol, 1995. 7(4): p. 349-56.

Braber, S., et al., Lung Cellular and Molecular Physiology, 2011. 300(2): p. L255-65.

Callow, K. A., et al., Clinical allergy, 1988. 18(2): p. 119-29.
Capra et al., Curr Med Chem, 2006. 13(26): p. 3213-26.
Carpagnano et al., Am J Respir Crit Care Med, 2003. 167(8): p. 1109-12.
Chibana et al., J Immunol, 2003. 170(8): p. 4290-5.
Cromwell et al., Adv Prostaglandin Thromboxane Leukot Res, 1982. 9: p. 251-7.
Del Prete et al., Blood, 2007. 109(2): p. 626-31.
Diaz-Gonzalez, F., et al., Ann Rheum Dis, 2007. 66(5): p. 628-32.
Ellis et al., Am J Respir Crit Care Med, 1994. 149(1): p. 118-22.
Espinosa et al., J Allergy Clin Immunol, 2003. 111(5): p. 1032-40.
Francis, M. F., et al., Pharmaceutical research, 2005b. 22(2): p. 209-19.
Francis, M. F., M. Cristea, and F. M. Winnik, Biomacromolecules, 2005a. 6(5): p. 2462-7.
Fretland et al., Inflammation, 1995. 19(2): p. 193-205.
Fretland et al., Inflammation, 1989. 13(5): p. 601-5.
Gaggar, A., et al., The open respiratory medicine journal, 2010. 4: p. 32-8.
Gaudreault et al., Prostaglandins Other Lipid Mediat, 2005. 75(1-4): p. 25-34.
Goldman, D. W., et al., J Immunol, 1986. 137(6): p. 1971-6.
Hardison, M. T., et al., J Immunol, 2009. 182(7): p. 4423-31.
Hawkey, C. J., et al., Gastroenterology, 1997. 112(3): p. 718-24.
Hicks, A., et al., Prostaglandins & other lipid mediators, 2010. 92(1-4): p. 33-43.
Hubbard et al., J Clin Invest, 1991. 88(3): p. 891-7.
Hullot et al., Arzneimittelforschung, 1997. 47(1): p. 51-8.
Jackson et al., J Pharmacol Exp Ther, 1999. 288(1): p. 286-94.
Jackson, P. L., et al., European journal of pharmacology, 2011.
Jiang et al., Bioorg Med Chem Lett, 2008. 18(24): p. 6549-52.
Kostikas, K., et al., Chest, 2005. 127(5): p. 1553-9.
Lawrence et al., Clin Exp Immunol, 1992. 89(2): p. 321-4.
Lawrence et al., Lancet, 1993. 342(8869): p. 465-9.
Lawrence et al., Clin Exp Immunol, 1994. 98(1): p. 12-6.
Linsel-Nitschke et al., Clin Sci (Lond), 2008. 115(10): p. 309-15.
Lobos et al., Dig Dis Sci, 1987. 32(12): p. 1380-8.
Loick, H. M. and J. L. Theissen, Anasthesiologie, Intensivmedizin, Notfallmedizin, Schmerztherapie: AINS, 1994. 29(1): p. 3-9.
Maycock et al., J Biol Chem, 1982. 257(23): p. 13911-4.
Mehta et al., Circulation, 1989. 79(3): p. 549-56.
Mehta, J. L., et al., Prostaglandins Leukot Med, 1987. 29(2-3): p. 259-67. Merkus, F. W., et al., Adv Drug Deliv Rev, 1999. 36(1): p. 41-57.
Nielsen et al., Scand J Clin Lab Invest, 1987. 47(6): p. 605-11.
O'Driscoll et al., Clin Exp Immunol, 1984. 55(2): p. 397-404.
Peters-Golden et al., Am J Respir Crit Care Med, 2002. 165(2): p. 229-35.
Pettersson et al., J Leukoc Biol, 2005. 77(6): p. 1018-25.
Profita et al., Am J Physiol Cell Physiol, 2000. 279(4): p. C1249-58.
Profita et al., Allergy, 2005. 60(11): p. 1361-9.
Radeau et al., Prostaglandins Leukot Essent Fatty Acids, 1990.41(2): p. 131-8.
Roberts, W. G., et al., Gastroenterology, 1997. 112(3): p. 725-32.
Sayers et al., Clin Exp Allergy, 2003. 33(8): p. 1103-10.
Schmitt-Grohe, S. and S. Zielen, Paediatric drugs, 2005. 7(6): p. 353-63.
Scott et al., Clin Diagn Lab Immunol, 2004. 11(5): p. 936-41.
Senoh et al., Cardiovasc Res, 1993. 27(12): p. 2194-9.
Shim et al., J Immunol, 2006. 177(3): p. 1918-24.
Shim, Y. M., et al., American journal of physiology. Lung cellular and molecular physiology, 2010. 299(6): p. L749-59.
Showell et al., J Pharmacol Exp Ther, 1995. 273(1): p. 176-84.
Snelgrove, R. J., et al., Science, 2010. 330(6000): p. 90-4.
Sperling et al., Arthritis Rheum, 1992. 35(4): p. 376-84.
Sprague, R. S., et al., Prostaglandins, 1990. 39(4): p. 439-50.
Sprague, R. S., et al., Critical care clinics, 1989. 5(2): p. 315-29.
Stenson et al., J Biol Chem, 1984. 259(19): p. 11784-9.
Sun, R. Z., et al., Chin Med J (Engl), 1990. 103(7): p. 595-8.
Tanno et al., Am J Chin Med, 1988. 16(3-4): p. 145-54.
Tarlowe et al., J Immunol, 2003. 171(4): p. 2066-73.
Topol et al., Hum Mol Genet, 2006. 15 Spec No 2: p. R117-23.
Turner et al., J Clin Invest, 1996. 97(2): p. 381-7.
Vargaftig et al., Am J Respir Cell Mol Biol, 2003. 28(4): p. 410-9.
Wardlaw et al., J Allergy Clin Immunol, 1989. 84(1): p. 19-26.
Widegren, H., et al., Respiratory medicine, 2011. 105(7): p. 997-1006.
Wilborn et al., J Clin Invest, 1996. 97(8): p. 1827-36.
Xu, X., et al., PLoS One, 2011. 6(1): p. e15781.
Zheng, T., et al., J Clin Invest, 2000. 106(9): p. 1081-93.
Zhu et al., J Immunol, 2002. 168(6): p. 2953-62.
Zhu et al., J Clin Invest, 1999. 103(6): p. 779-88.
Zhu, Z., et al., J Immunol, 2002. 168(6): p. 2953-62.
Zhu, Z., et al., J Clin Invest, 1999. 103(6): p. 779-88.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to inhibit or treat inflammation, comprising: administering to a mammal in need thereof an amount of a composition having a compound of formula (I) effective to enhance or augment aminopeptidase activity of leukotriene A4 hydrolase,
wherein the compound of formula (I) is

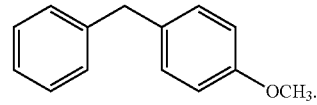 [SMILES: COc1ccc(Cc2ccccc2)cc1]

2. The method of claim 1 wherein the mammal is a human.

3. The method of claim 1 wherein the mammal has COPD, asthma, cystic fibrosis, inflammatory bowel disease, coronary artery disease, ARDS, acute lung injury, the common cold, influenza virus infection, or inflammatory arthritis.

4. The method of claim 1 wherein the administration is local.

5. The method of claim 1 wherein the administration is systemic.

6. The method of claim 1 wherein the administration is intravenous.

7. The method of claim 1 wherein the administration is by injection.

8. The method of claim 1 wherein the composition is intranasally administered.

9. The method of claim 1 wherein the composition comprises a compound of formula (I) and a pharmaceutically acceptable carrier.

10. The method of claim 9 wherein the carrier comprises liposomes.

11. The method of claim 9 wherein the carrier comprises nanoparticles or microparticles.

12. The method of claim 9 wherein the carrier comprises cyclic oligosaccharides.

13. The method of claim 1 wherein the effective amount of the composition of formula (I) inhibits the conversion of $LTA_4$ to a LTB.

14. The method of claim 13 wherein the LTB is $LTB_4$.

15. The method of claim 1 wherein the compound of formula (I) is in an inclusion complex with a macromolecular entity comprising a polysaccharide.

16. The method of claim 15 wherein the polysaccharide comprises a cyclodextrin.

17. The method of claim 16 wherein the cyclodextrin is a 2-hydroxypropyl-β-cyclodextrin.

18. The method of claim 1 wherein the composition further comprises a cyclodextrin.

19. The method of claim 18 wherein the cyclodextrin is 2-hydroxypropyl-β-cyclodextrin.

* * * * *